United States Patent
Rothbauer et al.

(10) Patent No.: US 7,717,774 B2
(45) Date of Patent: May 18, 2010

(54) STERILE FILLING ARRANGEMENT

(75) Inventors: Juergen Rothbauer, Michelfeld (DE); Mark Walter Diehl, Pocono Summit, PA (US); Wolfgang Boeck, Schwaebisch Hall (DE)

(73) Assignee: inova pharma systems GmbH, Schwaebisch Hall (DE)

( * ) Notice: Subject to any disclaimer, the term of this patent is extended or adjusted under 35 U.S.C. 154(b) by 0 days.

(21) Appl. No.: 11/138,791

(22) Filed: May 25, 2005

(65) Prior Publication Data
US 2006/0003685 A1    Jan. 5, 2006

(30) Foreign Application Priority Data
May 27, 2004    (DE) .................... 10 2004 026 883

(51) Int. Cl.
*B01L 1/04* (2006.01)
*F24F 7/06* (2006.01)
*B08B 15/02* (2006.01)

(52) U.S. Cl. .................... 454/187; 454/57; 454/66; 55/385.2

(58) Field of Classification Search .............. 454/56, 454/187, 57, 66; 55/385.2
See application file for complete search history.

(56) References Cited

U.S. PATENT DOCUMENTS

| | | | | |
|---|---|---|---|---|
| 3,339,992 A | * | 9/1967 | Trexler | 312/3 |
| 3,616,624 A | * | 11/1971 | Marsh | 55/472 |
| 3,782,265 A | * | 1/1974 | Pielkenrood et al. | 454/187 |
| 4,202,676 A | * | 5/1980 | Pelosi et al. | 96/416 |
| 4,319,899 A | * | 3/1982 | Marsh | 55/416 |
| 4,566,293 A | * | 1/1986 | Arner et al. | 62/51.1 |
| 4,723,480 A | * | 2/1988 | Yagi et al. | 454/57 |
| 5,259,812 A | * | 11/1993 | Kleinsek | 454/57 |
| 5,316,560 A | * | 5/1994 | Krone-Schmidt et al. | 55/385.2 |
| 5,441,708 A | * | 8/1995 | Diccianni et al. | 422/292 |
| 5,487,768 A | * | 1/1996 | Zytka et al. | 55/385.2 |
| 5,522,767 A | * | 6/1996 | Rertsche et al. | 454/187 |
| 5,783,156 A | * | 7/1998 | Renzi et al. | 422/292 |
| 5,892,200 A | * | 4/1999 | Kendall et al. | 219/201 |

(Continued)

FOREIGN PATENT DOCUMENTS

DE    333 73 98 A1    4/1984

(Continued)

OTHER PUBLICATIONS

Swain, Erik, Barrier Isolators versus RABS, Pharmaceutical & Medical Packaging News, Copyright 2002.

*Primary Examiner*—Steven B McAllister
*Assistant Examiner*—Patrick F. O'Reilly, III
(74) *Attorney, Agent, or Firm*—Boyle Fredrickson, S.C.

(57) ABSTRACT

An arrangement for the sterile, aseptic production and/or filling of pharmaceutical products contains a housing which, with the exception of an inlet and an outlet with a clearly defined cross-section, is closed in an airtight manner. Through the air inlet air is forced via a filter into the interior of the housing. The air passes out of the housing through the air outlet or channels. The size of the cross-section of the air outlet and the performance of the ventilating device are matched in such a way that within the interior of the housing there is a laminar unidirectional or combined airflow and a constant overpressure with respect to the pressure outside the housing.

10 Claims, 2 Drawing Sheets

U.S. PATENT DOCUMENTS

| | | | | |
|---|---|---|---|---|
| 5,912,184 | A * | 6/1999 | Young | 438/692 |
| 5,997,399 | A * | 12/1999 | Szatmary | 454/187 |
| 6,010,400 | A * | 1/2000 | Krainiak et al. | 454/187 |
| 6,095,918 | A * | 8/2000 | Arroyo et al. | 454/188 |
| 6,183,358 | B1 * | 2/2001 | Adair, Jr. | 454/187 |
| 6,364,762 | B1 * | 4/2002 | Kaveh et al. | 454/187 |
| 6,517,429 | B1 * | 2/2003 | O'Connell et al. | 454/56 |
| 2002/0074190 | A1 * | 6/2002 | McCrandall et al. | 187/244 |
| 2002/0121196 | A1 * | 9/2002 | Thakur et al. | 96/224 |
| 2002/0179602 | A1 * | 12/2002 | Cocker et al. | 220/6 |

FOREIGN PATENT DOCUMENTS

| | | | |
|---|---|---|---|
| DE | 343 75 43 | A1 | 5/1986 |
| DE | 363 22 76 | A1 | 4/1987 |
| DE | 197 26 222 | A1 | 12/1998 |
| DE | 299 15 190 | U1 | 1/2000 |
| DE | 199 52 651 | A1 | 6/2001 |
| EP | 0 096 336 | A2 | 12/1983 |
| JP | 62022935 | A * | 1/1987 |
| JP | 62123242 | A * | 6/1987 |
| JP | 04288428 | A * | 10/1992 |
| WO | WO01/70398 | A1 | 9/2001 |
| WO | WO02/051450 | A1 | 7/2002 |

* cited by examiner

STERILE FILLING ARRANGEMENT

BACKGROUND OF THE INVENTION

The invention relates to an arrangement for the sterile/aseptic production and/or filling of pharmaceutical products.

The term pharmaceutical products is understood to mean e.g. syringes, vials, carpules etc., which must be filled with a liquid or solid medium in an aseptic/sterile environment. For this purpose the containers must undergo several process steps, e.g. filling with a medium, closing and so on. All these processes must take place in a sterile and/or aseptic environment.

For this purpose it is known to use so-called isolators, i.e. arrangements where the process stations are contained in a closed casing. Access to the interior of said casing takes place by means of glove interventions, the inserting of components by RTP-Ports (Rapid Transfer Ports). The process stations are flooded with a directional airflow with a low particle content from an air supply unit and the air return takes place in closed ducts.

Such arrangements, devices or plants operate with high reliability, but are very expensive due to their complicated structure and have long validation periods and high validation volumina.

In addition, open systems are known, where the process stations are scavenged with a directional airflow with a low particle content from an air supply unit and without airflow return in closed ducts. Curtains and doors are provided to delimit the same from the surrounding area.

Open systems referred to in the technical literature as Restricted Access Barriers Systems (RABS) are also known. In simplified terms, these are isolator-like arrangements with openings at the bottom. Here again the process stations are scavenged with a directional, low particle content airflow from an air supply unit, but the airflow is not returned. These systems exclusively operate as displacement systems without an overpressure. The demarcation with respect to the surrounding area is provided by closable or sealable viewing windows and viewing doors. Access to such systems is only possible by glove interventions.

Open systems without air return are less expensive than isolators, but do not bring about the high product environment reliability and safety obtained with isolators.

The problem of the invention is to provide an arrangement for the sterile/aseptic production and/or filling of pharmaceutical products, which on the one hand ensures a high safety and reliability for the product to be handled similar to the isolators, but which on the other incurs lower costs and has shorter validation periods and lower validation volumina.

SUMMARY OF THE INVENTION

Thus, the arrangement or plant of the present invention contains a housing enclosing the process stations. This housing is closed with the exception of the air outlet, which can comprise several openings maybe provided as channels, and the air inlet for the ventilating device. The ventilating device forces air into the interior of the housing from which said air can escape through the air outlet having a clearly defined cross-section. A controlled overpressure relative to the environment of the housing is maintained in the latter. In similar manner as with isolators the access into the housing occurs by glove interventions and the insertion of components via RTP—Ports without influencing the overpressure in negative manner.

Through maintaining an overpressure it is ensured that a specific airflow occurs, without an expensive return being necessary.

According to a further development of the invention, it is possible according to the arrangement thereof to allow the air to move past in targeted manner the particular process station and for this purpose the arrangement can have air conducting or guiding means.

According to the invention, for further improving the result, the arrangement can have an air supply unit to ensure that there is a weak laminar unidirectional parallel flow or a combination of flows, which reliably forces downwards any particle still present.

As in the arrangement proposed by the invention the air is drawn from an air supply unit or from the environment of the arrangement, according to a further development the ventilating device can have a high performance suspended matter filter to ensure that the forced in air is particle free or at least contains few particles.

The ventilating device, which can comprise several parts, can in a further development of the invention be positioned in the housing. However, it is also possible to wholly or partly position it outside the housing.

Provision of directional airflow is a critical physical characteristic of the invention. According to the invention the airflow can be directed from top to bottom. It has been found that this is a particularly appropriate arrangement of the flow for ensuring that the particles are not whirled up.

To control the constant overpressure in the housing, the pressure control can act on the power of a motor driving the ventilating device fan.

However, it is also and also additionally possible for the pressure control to act on the opening cross-section of the air outlet or optionally also the air inlet.

According to the invention the arrangement can also have two or more housings, which are e.g. interconnected by locks. In the different housings can take place different processes for the production and/or filling of the pharmaceutical products. The housings can be constructed in the manner described and, as required, it is also possible for there to be differences in the overpressure maintained in the individual housings. The pressure difference between the different housings can also be controlled.

According to the invention, the high performance suspended, matter filter is positioned downstream of a fan belonging to the ventilating device.

It is also possible to position upstream of a fan of the ventilating device a filter, which filters the drawn in air beforehand. Optionally there can also be a cooling device for cooling the air, if it is necessary or appropriate to cool the actual process.

BRIEF DESCRIPTION OF THE DRAWINGS

Further features, details and advantages of the invention can be gathered from the claims and abstract, whose wording is by reference made into part of the content of the description, together with the following description of a preferred embodiment of the invention and the attached drawings, wherein show:

DETAILED DESCRIPTION

Figure 1:
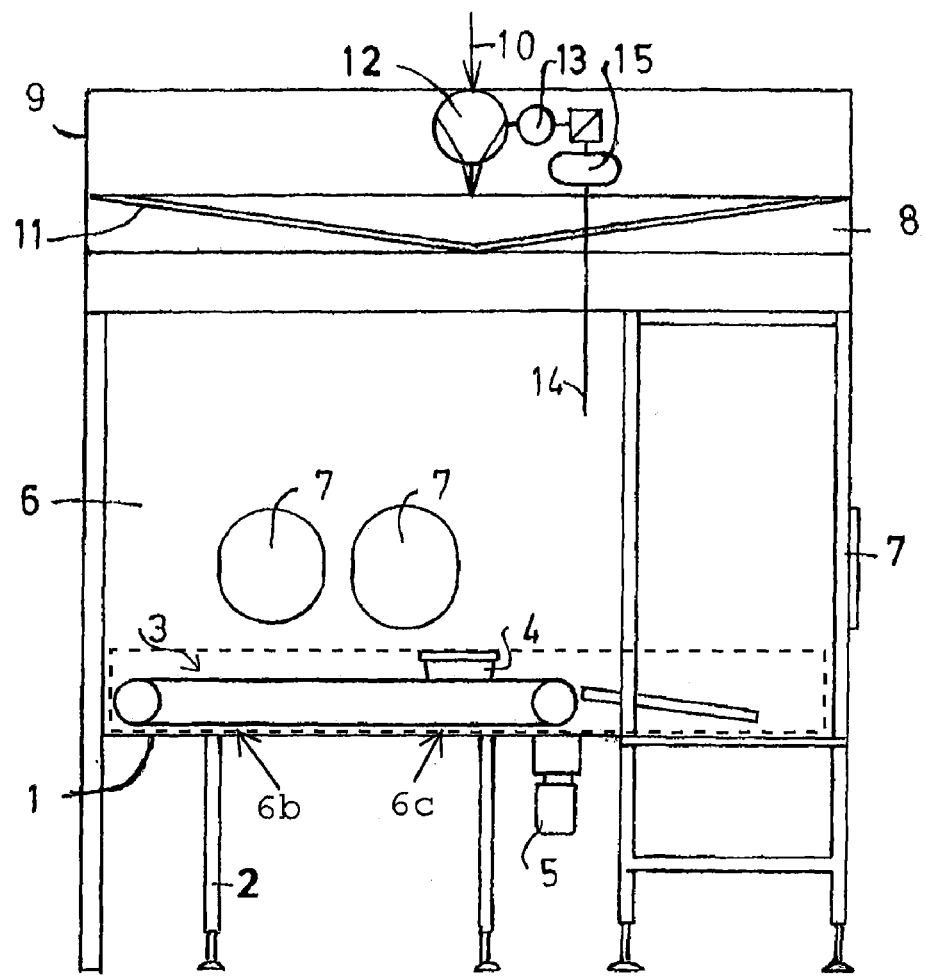
FIG. 1 Diagrammatically a side view of an arrangement according to the invention.

FIG. 1 shows a table plate 1, which is placed on a frame 2, which can comprise several parts.

As an example of one of the possible process stations on the table plate is placed a conveyor belt 3 used for the conveying of a container 4. The container 4 can e.g. contain several syringes in a holder. An electric motor 5, positioned below the table plate, is used for driving the conveyor belt.

On the table plate is placed a housing 6, which at its lower edge is tightly connected to said table plate 1. Into the housing lead glove interventions 7, which are only diagrammatically shown here. A glove intervention is also provided to the right in the front wall. At the top the housing is closed by a type of hood 8 and the connection between the housing 6 and the hood 8 is also airtight. In the lower area, e.g. on one or both front sides, all-around or also in the table plate 1 are provided openings 6b, 6c with a specific cross-section forming an air outlet from the housing 6. The upper hood 8 houses a ventilating device 9, which by means of a not shown filter draws its air from the environment in the direction of arrow 10 and delivers it downwards into the housing 6.

Immediately below the ventilating device, a high performance suspended matter filter 11 is positioned between the ventilating device 9 and the process station. The filter extends between the housing walls. Together with the air supply unit, it ensures a laminar, unidirectional parallel flow or a combination of an extremely low particle content airflow, which passes vertically from the top to the bottom into the interior of the housing 6. The flow passes out again from the aforementioned air outlet. With the aid of not shown air guidance means, the flow can be guided in such a way that it passes process stations, i.e. points where particles are to be led away.

The ventilating device 9 contains a fan 12 driven by a motor 13. In the interior of the housing 6 is provided a pressure sensor 14 acting on a control means of the motor 13. A regulating device 15 upstream of the motor 13 ensures that the pressure within the housing 6 is kept constant, e.g. at 0 to 30 Pascal overpressure with respect to the pressure outside the housing.

Instead of the control of the speed and therefore power of the motor 13 of fan 12, it would also be possible to control the cross-section of the air outlet from the housing-6 for regulating the overpressure in the interior of the latter.

Figure 2:
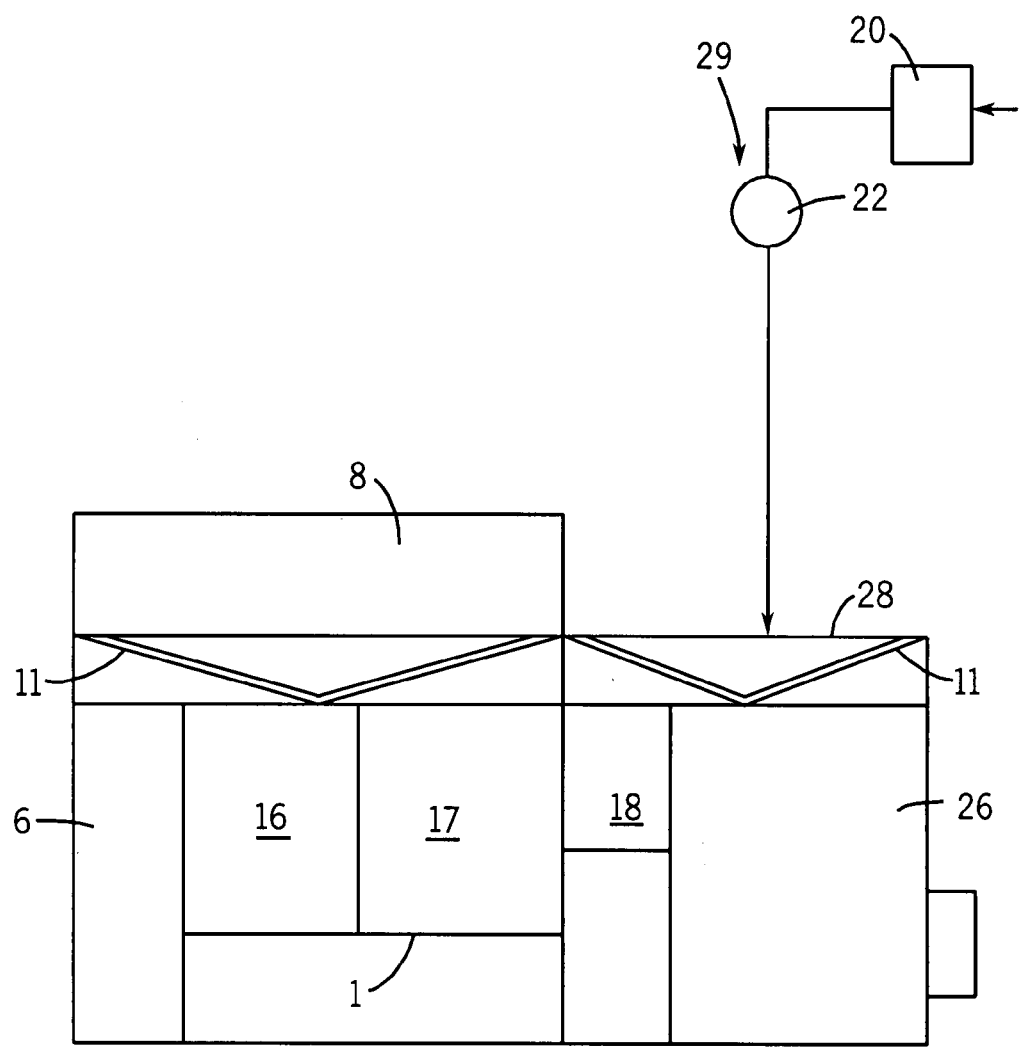
FIG. 2 in even more diagrammatic manner an arrangement with two housings.

FIG. 2 shows a possibility for an arrangement of several housings with the same or a similar structure. Thus, to the left FIG. 2 contains a housing 6 constructed in the manner described relative to FIG. 1. FIG. 2 e.g. constitutes a front view. The housing 6 contains two compartments 16, 17, whereof compartment 16 e.g. contains the conveyor belt 3 of FIG. 1. Compartment 17 can e.g. contain a station for removing the cover of the container 4.

Adjacent to the housing 6 is provided a second housing 26, a lock 18 being positioned between the two housings 6, 26. It is a lock having changeover doors. The packs opened in compartment 17 can e.g. be filled in housing 26 from a process station positioned there and then sealed. In much the same way as the left-hand housing 6, the housing 26 has an air supply unit and a high performance suspended matter filter 11. In this case the ventilating device with a fan 22 is positioned outside the housing 26. Therefore a line leads from the fan 22 of ventilating device 29 to an opening in the outer wall of the hood 28. The air drawn in by the fan 22 of ventilating device 29 can be cooled by a cooling device 20, which can also have the aforementioned inlet filter.

The invention claimed is:

1. Arrangement for the production or filling of pharmaceutical products, the arrangement having a housing with a housing portion that contains at least one process station for processing or filling pharmaceutical products, said process station including a powered means for conveying the pharmaceutical products within the housing portion, the housing having at least two glove openings in the housing portion for receiving two gloves in the housing portion, a ventilating device and an air supply unit for forcing air from outside the housing into the housing through an air inlet, an air outlet out of the housing with a defined cross-section, the air outlet being located in a lower area of the housing on at least one wall thereof, and a pressure regulating device with a pressure sensor disposed in the housing portion, the pressure regulating device maintaining a specific overpressure in the housing portion that contains the at least one process station and the at least two glove openings, wherein the housing is airtight when the gloves are received in the glove openings in the housing except for the air inlet, the ventilating device and the air outlet, which together allow a continuous, non-recirculating air flow from the air inlet through the housing and past the gloves when received within the housing, to the air outlet while still maintaining an aseptic, sterile environment within the housing for the production or filling of pharmaceutical products; and wherein the airflow produced by the ventilating device is directed from top to bottom in at least one of a laminar unidirectional parallel flow or a combination of flows, which forces downwards any particles that are present.

2. Arrangement according to claim 1, with an air temperature regulation for setting a predetermined air temperature in the housing.

3. Arrangement according to claim 1, having air guidance means to make the air flow past the process station in a targeted manner.

4. Arrangement according to claim 1, having a high performance suspended matter filter.

5. Arrangement according to claim 4, wherein the high performance suspended matter filter is positioned downstream of a fan of the ventilating device.

6. Arrangement according to claim 1, wherein the ventilating device is located in the housing.

7. Arrangement according to claim 1, wherein the ventilating device is at least partly located outside a hood of the housing.

8. Arrangement according to claim 1, wherein the pressure regulating device acts on the power of a motor driving a fan of the ventilating device.

9. Arrangement according to claim 1, in combination with a second arrangement that is linked by a lock chamber.

10. Arrangement according to claim 1, having a filter upstream of the ventilating device.

* * * * *